US00PP11259P

United States Patent [19]

Heims

[11] Patent Number: Plant 11,259

[45] Date of Patent: Mar. 7, 2000

[54] HEUCHERA PLANT NAMED 'CHAMPAGNE BUBBLES'

[75] Inventor: Dan M. Heims, Portland, Oreg.

[73] Assignee: Terra Nova Nurseries, Inc., Tigard, Oreg.

[21] Appl. No.: 09/048,920

[22] Filed: Mar. 26, 1998

[51] Int. Cl.[7] ..... A01H 5/00

[52] U.S. Cl. ..... Plt./263

[58] Field of Search ..... Plt./263

[56] References Cited

U.S. PATENT DOCUMENTS

P.P. 8,858 8/1994 Bloom ..... Plt./263
P.P. 10,441 6/1998 Bloom ..... Plt./263

*Primary Examiner*—Howard J. Locker
*Assistant Examiner*—Wendy A Baker
*Attorney, Agent, or Firm*—Klarquist Sparkman Campbell Leigh & Whinston, LLP

[57] ABSTRACT

A new and distinct hybrid of Heuchera characterized by lightly ruffled foliage, low habit, evergreen nature and several progressive bloomings of many small flowers that change color as they age from rose to white.

1 Drawing Sheet

The present invention relates to a new and distinct hybrid of Heuchera of the family Saxifragaceae which originated as a cross pollination of *Heuchera micrantha* 'Ruffles' and *Heuchera americana* 'Whirlwind'.

The new Heuchera is a result of a controlled cross of the aforementioned plants at Terra Nova Nursery, Inc., in Canby, Oreg. This hybrid was selected from a large selection of seedlings. Pollen and pod parents were retained to observe and compare their habit to the instant plant. The New variety has been reproduced only by asexual propagation (division and tissue culture). Each of the progeny exhibits identical characteristics to the original plant and is unlike any Heuchera offered by any American nursery or book as evidenced by the following characteristics:

(1) Summer, fall and winter: Lightly ruffled foliage, low habit, evergreen nature.

(2) Spring: Several progressive bloomings of many small flowers that change color as they age from rose to white.

Asexual propagation by division and tissue-culture as done in Tigard, Oreg., shows that the foregoing characteristics and distinctions come true to form and are established and transmitted through succeeding propagations.

BRIEF DESCRIPTION OF THE DRAWING

The drawing shows Heuchera 'Champagne Bubbles' in bloom in early May.

DETAILED PLANT DESCRIPTION

The following is a detailed description of the new Heuchera hybrid based on observations of specimens in Canby, Oreg. The color descriptions are all based on *The Royal Horticulural Society Colour Chart* and the *American Rhododendron Society publication,* "A Contribution Toward Standardization of Color Names in Horticulture."

Foliage:

*Type.*—Evergreen, herbaceous in a hard winter.
*Shape.*—Rounded undulate-cordate, 9-lobed.
*Length.*—5.2-6.5 cm.
*Width.*—6.5 cm.
*Petiole length.*—7.5–8.7 cm.
*Margins.*—Undulate: crenate-dentate; ciliolate.
*Apex.*—Broadly acute, lobed, serrate.

*Base.*—Cordate.
*Texture.*—Slightly rugose; exhibit short pubescence.
*Leaf arrangement.*—Basal clump.
*Venation.*—Reticulate.
*Panicles per two-year-old plant.*—32 to 42.
*Plant foliage height.*—26 cm. on a second year plant.
*Average spread of foliage.*—47 cm. on a second year plant at Canby, Oreg.

Flower:

*Flower stem girth.*—3.5 to 5 mm. tapering to 1 mm. at apex. Flower stems exhibit slight pubescence; no tendency towards fasciation observed.
*Petal count.*—5 petals.
*Petal shape.*—urn-shaped calyx, entire margin.
*Flower type.*—complete calyx tube, stamens not exserted.
*Flower size.*—0.4 cm.
*Flower number.*—100 to 200 (variable) per panicle.
*Blooming habit.*—Panicles to 56 cm. tall.
*Bloom period.*—In Oregon from late April to Early June. Intermittent rebloom has been observed.

Fruit: A dehiscent capsule; the plant is fertile.

Color characteristics:

*Foliage.*—Mature leaves, upper surface: R.H.S. 139A Green Group (Dark Yellowish Green ARS) to R.H.S. 141B Green Group (Deep Yellowish Green ARS). Lower surface: R.H.S. 147C Yellow Green Group (Moderate Yellow Green ARS). No seasonal changes in color of foliage.
*Flower stems.*—R.H.S. 187B Grey Purple Group fading to R.H.S. 152A Yellow Green Group.
*Flowers.*—65A Red-Purple Group (moderate purplish-pink fading to 155D White Group (yellowish white).
*Fruit.*—Capsules: R.H.S. 152A Yellow Green Group.
*Frost/low temperature tolerance.*—Frost tolerance is set at Zone 4 (−30 to −40 degrees F.). Plant will remain evergreen in Zones 5 (−30 to −20 degrees F.) and above.

DESCRIPTION OF PARENT PLANTS

*Heuchera micrantha* 'Ruffles' (unpatented) is described in the Terra Nova Nurseries, Inc., Portland, Oreg., 1998 catalog as having heavily ruffled hirsute foliage and white panicles of flowers. Heuchera 'Whirlwind' (unpatented) is described in the same catalog as having foliage that is remarkably fluted and crested, and having pink and white flowers. No other Heuchera in commerce resembles Heuchera 'Champagne Bubbles'.

I claim:

1. A new and distinct hybrid of Heuchera plant substantially as shown and described, characterized by: Lightly ruffled foliage, low habit, evergreen nature and several progressive bloomings of many small flowers that change color as they age from rose to white.

* * * * *

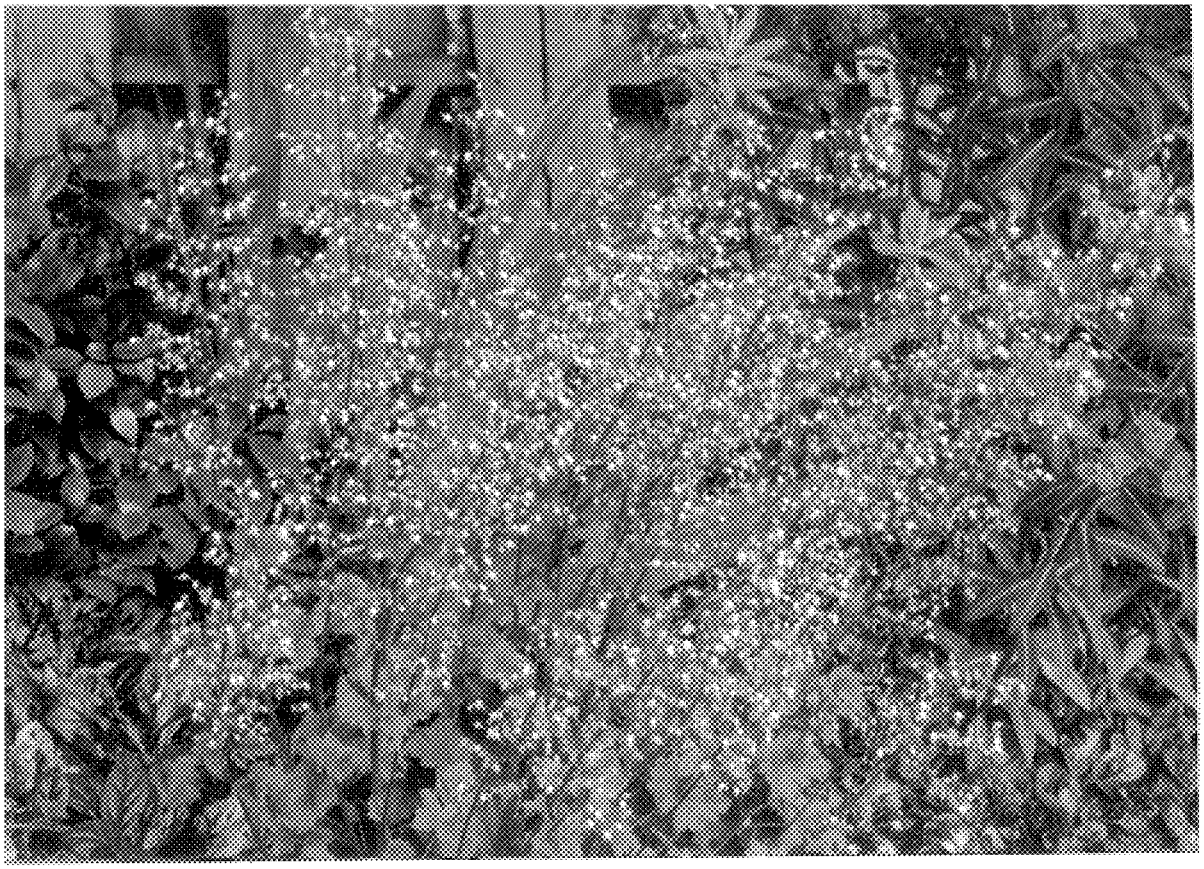

UNITED STATES PATENT AND TRADEMARK OFFICE

CERTIFICATE OF CORRECTION

PATENT NO. : Plant 11,259
DATED : March 7, 2000
INVENTOR(S) : Dan M. Heims

It is certified that error appears in the above-identified patent and that said Letters Patent is hereby corrected as shown below:

Col. 2, line 5, cancel "panicles per two-year old plant. --32 to 42."
Col. 2, between lines 17 and 18, insert
--Panicles per two-year old plant.--32 to 42.--

Signed and Sealed this

Fifteenth Day of May, 2001

*Attest:*

Nicholas P. Godici

NICHOLAS P. GODICI

*Attesting Officer*

*Acting Director of the United States Patent and Trademark Office*